US012210904B2

(12) United States Patent
Eda et al.

(10) Patent No.: US 12,210,904 B2
(45) Date of Patent: Jan. 28, 2025

(54) HYBRIDIZED STORAGE OPTIMIZATION FOR GENOMIC WORKLOADS

(71) Applicant: International Business Machines Corporation, Armonk, NY (US)

(72) Inventors: Sasikanth Eda, Vijayawada (IN); Sandeep R. Patil, Pune (IN); William W. Owen, Tucson, AZ (US); Kumaran Rajaram, Fairfax, VA (US)

(73) Assignee: International Business Machines Corporation, Armonk, NY (US)

( * ) Notice: Subject to any disclaimer, the term of this patent is extended or adjusted under 35 U.S.C. 154(b) by 522 days.

(21) Appl. No.: 16/023,091

(22) Filed: Jun. 29, 2018

(65) Prior Publication Data

US 2020/0004592 A1   Jan. 2, 2020

(51) Int. Cl.
*G06F 3/06* (2006.01)
*G06F 9/38* (2018.01)
(Continued)

(52) U.S. Cl.
CPC .......... *G06F 9/5016* (2013.01); *G06F 3/0611* (2013.01); *G06F 3/065* (2013.01);
(Continued)

(58) Field of Classification Search
CPC ...... G06F 9/5016; G06F 9/3867; G06F 3/067; G06F 3/065; G06F 3/0611; G16B 20/00; G16B 50/00
(Continued)

(56) References Cited

U.S. PATENT DOCUMENTS

| 5,537,562 A * | 7/1996 | Gallup ...................... G06F 7/57 |
| | | 712/234 |
| 9,645,885 B2 | 5/2017 | De Schrijver |

(Continued)

FOREIGN PATENT DOCUMENTS

| CN | 107204969 A1 | 9/2017 | |
| WO | WO2017153456 A1 | 9/2017 | |
| WO | WO-2018068828 A1 * | 4/2018 | ............. G06F 17/16 |

OTHER PUBLICATIONS

Kelsey Suyehira, Using DNA for Data Storage Encoding and Decoding Algorithm Development, Dec. 2018, pp. 1-3, Boise State University Theses and Dissertations (Year: 2018).*

(Continued)

*Primary Examiner* — Titus Wong
(74) *Attorney, Agent, or Firm* — Kimberly Zillig; Ryan Mason & Lewis LLP (57) ABSTRACT

A method for more efficiently storing genomic includes designating multiple different data storage techniques for storing genomic data generated by a genomic pipeline. The method further identifies a file, made up of multiple blocks, generated by the genomic pipeline. The method determines which data storage technique is most optimal to store each block of the file. In doing so, the method may consider the type of the file, the stage of the genomic pipeline that generated the file, the access frequency for blocks of the file, the most accessed blocks of the file, and the like. The method stores each block using the data storage technique determined to be most optimal after completion of a designated stage of the genomic pipeline, such that blocks of the file are stored using several different data storage techniques. A corresponding system and computer program product are also disclosed.

20 Claims, 12 Drawing Sheets

(51) Int. Cl.
    *G06F 9/50*         (2006.01)
    *G16B 20/00*      (2019.01)
    *G16B 50/00*      (2019.01)

(52) U.S. Cl.
    CPC ............ *G06F 3/067* (2013.01); *G06F 9/3867* (2013.01); *G16B 20/00* (2019.02); *G16B 50/00* (2019.02)

(58) Field of Classification Search
    USPC .......................................................... 710/74
    See application file for complete search history.

(56) References Cited

U.S. PATENT DOCUMENTS

| | | | |
|---|---|---|---|
| 10,884,981 B1* | 1/2021 | Kakita | G06F 16/144 |
| 2003/0188097 A1* | 10/2003 | Holland | G06F 11/1076 |
| | | | 714/E11.034 |
| 2012/0089339 A1* | 4/2012 | Ganeshalingam | G06F 16/22 |
| | | | 702/19 |
| 2012/0089603 A1* | 4/2012 | Ganeshalingam | G16B 50/00 |
| | | | 707/736 |
| 2013/0339818 A1 | 12/2013 | Baker | |
| 2015/0286495 A1* | 10/2015 | Lee | G06F 16/164 |
| | | | 718/102 |
| 2015/0286656 A1* | 10/2015 | Djam | G16B 50/30 |
| | | | 707/827 |
| 2016/0072800 A1 | 3/2016 | Soon-shiong et al. | |
| 2016/0203155 A1 | 7/2016 | Akelbein et al. | |
| 2016/0301707 A1 | 10/2016 | Cheng et al. | |
| 2016/0357437 A1* | 12/2016 | Doerner | G06F 3/0613 |
| 2017/0060711 A1* | 3/2017 | Davis | G06F 3/064 |
| 2017/0123692 A1* | 5/2017 | Erdmann | G06F 3/0685 |
| 2017/0126704 A1 | 5/2017 | Nandha Premnath et al. | |
| 2017/0147437 A1* | 5/2017 | Borlick | G06F 11/1088 |
| 2017/0187390 A1* | 6/2017 | Le Scouarnec | G06F 3/0661 |
| 2017/0213038 A1 | 7/2017 | Shabtai et al. | |
| 2017/0286594 A1* | 10/2017 | Reid | G16B 20/00 |
| 2017/0316154 A1* | 11/2017 | Fitch | G16B 30/10 |
| 2019/0050302 A1* | 2/2019 | Juniwal | G06F 3/0689 |
| 2019/0073265 A1* | 3/2019 | Brennan | G06F 3/061 |
| 2019/0214111 A1* | 7/2019 | Alberti | G16B 45/00 |
| 2020/0042735 A1* | 2/2020 | Baluch | G06F 16/2365 |

OTHER PUBLICATIONS

Azat Akhmetov et al., BMC Biotechnology, A highly parallel strategy for storage of digital information in living cells, Oct. 17, 2018, Article No. 64, pp. 1-48 (Year: 2018).*

Azat Akhmetov et al. BMC Biotechnology, A highly parallel strategy for storage of digital information in living cells, Oct. 17, 2018, Article No. 65, pp. 1-48 (Year: 2018).*

Plank, J.S. (2013) "Erasure Codes for Storage Systems—A Brief Primer," https://www.usenix.org/system/files/login/articles/10_plank-online.pdf, 8 pgs. < Retrieved Jan. 19, 2024>.

Schmeier, S. (2020) "Computational Genomics Tutorial," 90 pgs, https://genomics-fungi.sschmeier.com/ <Retrieved Jan. 19, 2024>.

Sheldon, R. "erasure coding," https://www.techtarget.com/searchstorage/definition/erasure-coding, 5 pgs. <Retrieved Jan. 19, 2024>.

Stephens, ZD, et al. (2015) Big Data: Astronomical or Genomical? PLoS Biol 13(7): e1002195. https://doi.org/10.1371/journal.pbio.1002195.

Wong, J. et al. (2018), "IBM Spectrum Scale Best Practices for Genomics Medicine Workloads," https://www.redbooks.ibm.com/abstracts/redp5479.html, 78 pgs.

* cited by examiner

```
{
    "rule-attrs": {
        "stage-1": {
            "name": "quality_assessment",
            "filetypes": ["fastq", "fa", "fq", "trimmed"],
            "dir_location": "data",
            "read_frequency": "Low",
            "access_blocks": ["header", "metadata"],
            "post-optimize": "assembly"
        },
        "stage-2": {
            "name": "assembly",
            "filetypes": ["tar,gz", "fastq"],
            "dir_location": "data/assembly",
            "read_frequency": "Moderate",
            "access_blocks": ["header", "data"],
            "post-optimize": "variant_calling"
        },
            - - - - -
            - - - - -
        "stage-10": {
            "name": "variants_of_interest",
            "filetypes": ["config", "gif", "fa", "vcf"],
            "dir_location": "analysis/results",
            "read_frequency": "High",
            "access_blocks": ["header", "metadata", "data"],
            "post-optimize": "Never"
        },
    }
}
```

```
{
    "group-1": {
        "name": "replica-1",
        "type": "sync block replication",
        "disks": ["flash1", "flash2", "sas1", "sas2"],
    },
    "group-2": {
        "name": "replica-2",
        "type": "async block replication",
        "disks": ["flash1", "flash2", "sas1", "sas2"],
    },
    "group-3": {
        "name": "ec-1",
        "type": "ec-scheme_9/11",
        "disks": ["sda1", "sda2", ... , "sda11"],
    },
    "group-4": {
        "name": "ec-2",
        "type": "ec-scheme_6/9",
        "disks": ["sda1", "sda2", ... , "sda9"],
    }
}
```

| Name | File XYZ |
|---|---|
| Size | 512 |
| User ID (Ownership) | 1000 |
| Creation Time | 1346426869 |
| - - - - | - - - - |
| Block Addresses | x0018, x0022, x0044, G001, x0098 |

```
"G001":
{
        "type": "sync block replication",
        "blocks": {[x001, x002, x004], [x100, x101, x102]}
}

"G002":
{
        "type": "async block replication",
        "blocks": {[x401, x402, x404], [x900, x901, x902]}
}

"G003":
{
        "type": "ec_scheme_9/11",
        "blocks": [x200, x201, x202, x203, x204, x205, x206, x207, x208, x209, x210, x211]
}

"G004":
{
        "type": "ec_scheme_6/9",
        "blocks": [x600, x601, x602, x603, x604, x605, x606]
}
```

HYBRIDIZED STORAGE OPTIMIZATION FOR GENOMIC WORKLOADS

BACKGROUND

Field of the Invention

This invention relates to systems and methods for optimizing storage for specialized workloads.

Background of the Invention

Genomics is a branch of biotechnology that focuses on genomes. A genome is an organism's complete set of DNA and contains all the information that is needed to build and maintain that organism. A gene is a segment of the DNA that contains information on assembling the building blocks for one specific protein, which are the functional molecules of a cell. Genomics involves applying the techniques of genetics and molecular biology to sequence, analyze, or modify the DNA of an organism. It finds its use in many fields, such as diagnostics, personalized healthcare, agricultural innovation, forensic science, and the like.

Genomics requires a significant focus on big data management as the sequencing of the genome results in the production of large amounts of data. Genomics data analysis requires the following processing steps: (1) sequencers convert the physical sample to raw data; (2) raw data is arranged in a sequence corresponding to the genome; and (3) analytics (for example, matching mutations with certain diseases) is performed. Raw data of a single sample is up to a few hundred gigabytes of data. For average organizations, the total data that needs to be acquired, stored, analyzed, managed, and archived can be on the order of tens of petabytes.

IT administrators, physicians, data scientists, researchers, bioinformaticians, and other professionals who are involved in the genomics workflow need the right foundation to achieve their objectives efficiently while improving patient care and outcomes. Thus, it is important to understand the different stages of the genomics workload and the key characteristics of it. A typical genome pipeline involves the following stages: collecting of sequencing output, quality assessment/control, genome assembly, read mapping, taxonomic investigation, variant calling, genome annotation, orthology and phylogeny, variant-of-interest, and sharing or visualization of results. Each stage exhibits different data/metadata read and write characteristics as well as generates files of different types, sizes, and importance. These files may be used in subsequent stages or may be discarded or retained after a single stage is executed.

In view of the foregoing, particularly in view of the large storage requirements for genomic data, systems and methods are needed to efficiently store genomic data without compromising I/O performance, reliability, and/or data redundancy. Ideally, such systems and methods will be optimally tailored to the genomic workload.

SUMMARY

The invention has been developed in response to the present state of the art and, in particular, in response to the problems and needs in the art that have not yet been fully solved by currently available systems and methods. Accordingly, systems and methods have been developed to more efficiently store genomic data. The features and advantages of the invention will become more fully apparent from the following description and appended claims, or may be learned by practice of the invention as set forth hereinafter.

Consistent with the foregoing, a method for more efficiently storing genomic data is disclosed. In one embodiment, such a method includes designating multiple different data storage techniques for storing genomic data generated by a genomic pipeline. The method further identifies a file, made up of multiple blocks, generated by the genomic pipeline. The method determines which data storage technique is most optimal to store each block of the file. In doing so, the method may consider the type of the file, the stage of the genomic pipeline that generated the file, the access frequency for blocks of the file, the most accessed blocks of the file, and the like. The method stores each block using the data storage technique determined to be most optimal after completion of a designated stage of the genomic pipeline, such that blocks of the file are stored using several different data storage techniques.

A corresponding system and computer program product are also disclosed and claimed herein.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the embodiments of the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

The present invention may be embodied as a system, method, and/or computer program product. The computer program product may include a computer readable storage medium (or media) having computer readable program instructions thereon for causing a processor to carry out aspects of the present invention.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on a user's computer, partly on a user's computer, as a stand-alone software package, partly on a user's computer and partly on a remote computer, or entirely on a remote computer or server. In the latter scenario, a remote computer may be connected to a user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

Figure 1:
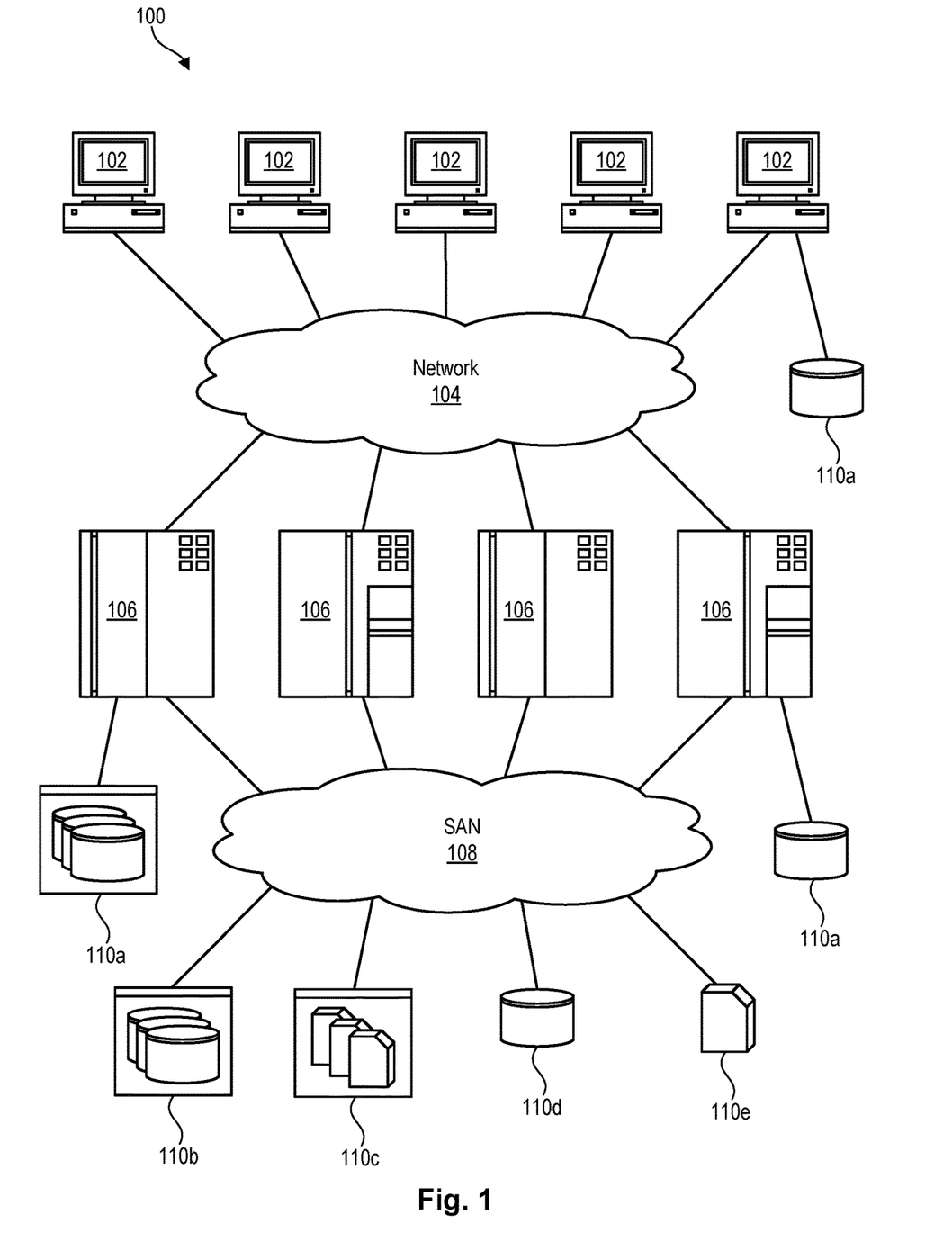
FIG. 1 is a high-level block diagram showing one example of a network environment in which systems and methods in accordance with the invention may be implemented.

Referring to FIG. 1, one example of a network environment 100 is illustrated. The network environment 100 is presented to show one example of an environment where systems and methods in accordance with the invention may be implemented. The network environment 100 is presented by way of example and not limitation. Indeed, the systems and methods disclosed herein may be applicable to a wide variety of different network environments, in addition to the network environment 100 shown.

As shown, the network environment 100 includes one or more computers 102, 106 interconnected by a network 104. The network 104 may include, for example, a local-area-network (LAN) 104, a wide-area-network (WAN) 104, the Internet 104, an intranet 104, or the like. In certain embodiments, the computers 102, 106 may include both client computers 102 and server computers 106 (also referred to herein as "host systems" 106). In general, the client computers 102 initiate communication sessions, whereas the server computers 106 wait for and execute requests from the client computers 102. In certain embodiments, the computers 102 and/or servers 106 may connect to one or more internal or external direct-attached storage systems 110a (e.g., arrays of hard-disk drives, solid-state drives, tape drives, etc.). These computers 102, 106 and direct-attached storage systems 110a may communicate using protocols such as ATA, SATA, SCSI, SAS, Fibre Channel, or the like.

The network environment 100 may, in certain embodiments, include a storage network 108 behind the servers 106, such as a storage-area-network (SAN) 108 or a LAN 108 (e.g., when using network-attached storage). This network 108 may connect the servers 106 to one or more storage systems, such as arrays 110b of hard-disk drives or solid-state drives, tape libraries 110c, individual hard-disk drives 110d or solid-state drives 110d, tape drives 110e, CD-ROM libraries, or the like. To access a storage system 110, a host system 106 may communicate over physical connections from one or more ports on the host 106 to one or more ports on the storage system 110. A connection may be through a switch, fabric, direct connection, or the like. In certain embodiments, the servers 106 and storage systems 110 may communicate using a networking standard such as Fibre Channel (FC).

Figure 2:
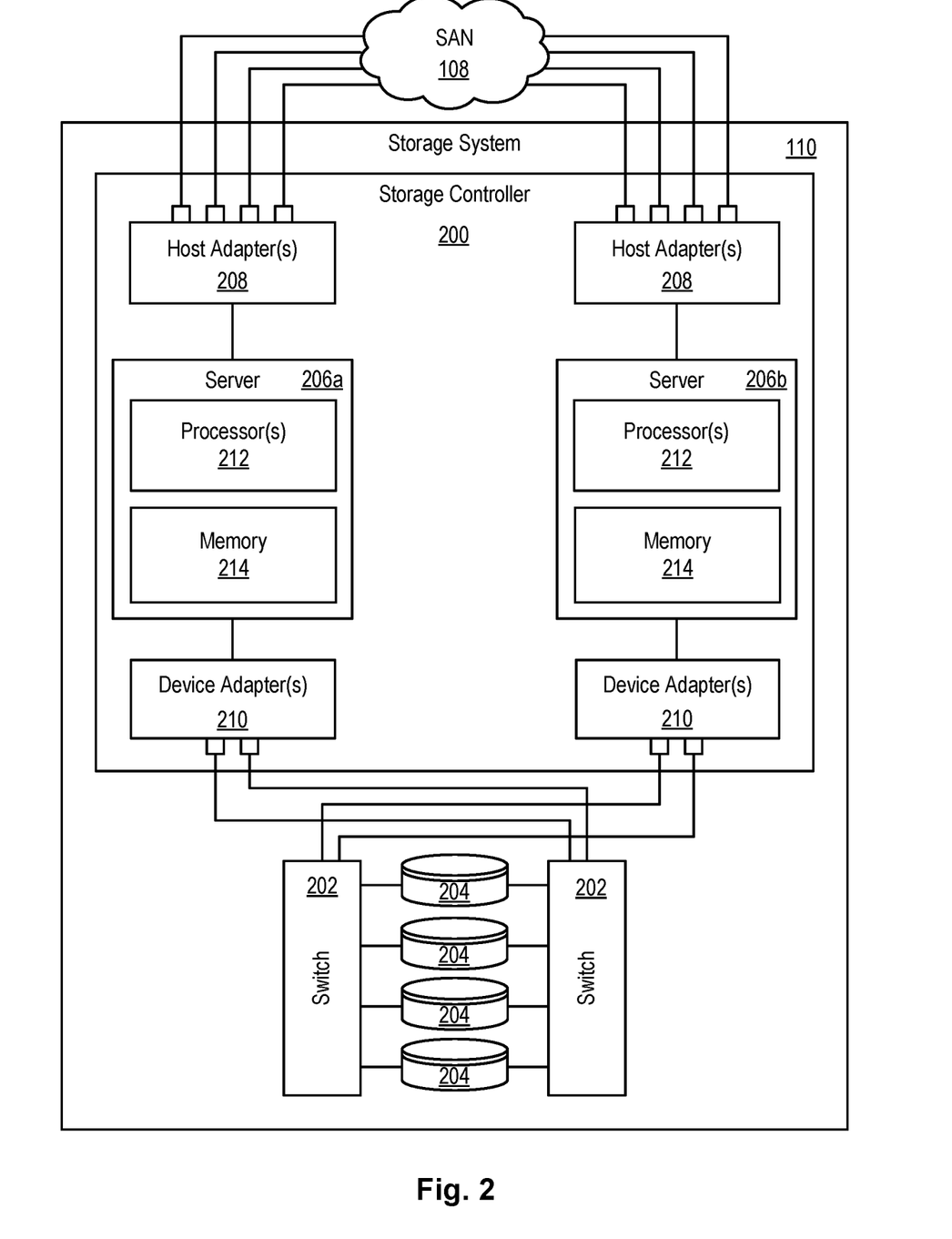
FIG. 2 is a high-level block diagram showing one example of a storage system in the network environment of FIG. 1.

Referring to FIG. 2, one embodiment of a storage system 110 containing an array of hard-disk drives 204 and/or solid-state drives 204 is illustrated. As shown, the storage system 110 includes a storage controller 200, one or more switches 202, and one or more storage drives 204, such as hard disk drives 204 or solid-state drives 204 (such as flash-memory-based drives 204). The storage controller 200 may enable one or more hosts 106 (e.g., open system and/or mainframe servers 106 running operating systems such z/OS, zVM, or the like) to access data in the one or more storage drives 204.

In selected embodiments, the storage controller 200 includes one or more servers 206. The storage controller 200 may also include host adapters 208 and device adapters 210 to connect the storage controller 200 to host devices 106 and storage drives 204 respectively. Multiple servers 206a, 206b may provide redundancy to ensure that data is always available to connected hosts 106. Thus, when one server 206a fails, the other server 206b may pick up the I/O load of the failed server 206a to ensure that I/O is able to continue between the hosts 106 and the storage drives 204. This process may be referred to as a "failover."

In selected embodiments, each server 206 may include one or more processors 212 and memory 214. The memory 214 may include volatile memory (e.g., RAM) as well as non-volatile memory (e.g., ROM, EPROM, EEPROM, hard disks, flash memory, etc.). The volatile and non-volatile memory may, in certain embodiments, store software modules that run on the processor(s) 212 and are used to access data in the storage drives 204. These software modules may manage all read and write requests to logical volumes in the storage drives 204.

One example of a storage system 110 having an architecture similar to that illustrated in FIG. 2 is the IBM DS8000™ enterprise storage system. The DS8000™ is a high-performance, high-capacity storage controller providing disk storage that is designed to support continuous operations. Nevertheless, the systems and methods disclosed herein are not limited to operation with the IBM DS8000™ enterprise storage system 110, but may operate with any comparable or analogous storage system 110, regardless of the manufacturer, product name, or components or component names associated with the system 110. Furthermore, any storage system that could benefit from one or more embodiments of the invention is deemed to fall within the scope of the invention. Thus, the IBM DS8000™ is presented by way of example and is not intended to be limiting.

Figure 3:
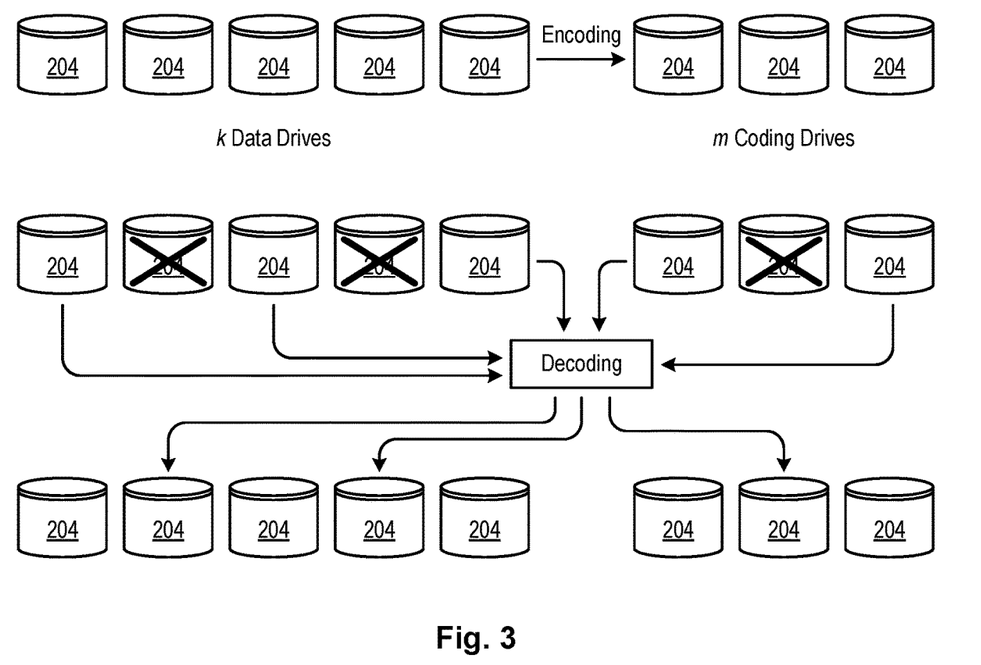
FIG. 3 is a high-level block diagram showing an example of an erasure coding data storage technique.

Referring to FIG. 3, as previously mentioned, genomics requires a significant focus on big data management as the sequencing of the genome results in the production of large amounts of data. Various different techniques may be used to store and protect genomic data. For example, data replication may be used to store a file at a primary location, and then replicate a copy of the file to a secondary and possibly tertiary location. Although this data storage technique may be effective, it consumes a large amount of storage space as each file may consume double or triple its size in storage capacity once it is replicated across all locations.

Erasure coding is another technique for storing and protecting data. Using this technique, data may be broken into fragments (the number of fragments may depend on the selected erasure code scheme), expanded, encoded with redundant data pieces, and stored across a set of different locations or storage media. One example of this technique is illustrated in FIG. 3. Using a storage system 110 that includes n storage drives 204, the storage drives 204 may be partitioned into k storage drives 204 that store user data and m storage drives 204 that store coding information. The acts of encoding and decoding are shown in FIG. 3. With encoding, the contents of the k data storage drives 204 are used to calculate the contents of the m coding storage drives 204. When up to m storage drives 204 fail, their contents may be decoded and reproduced from the surviving storage drives 204, as shown in FIG. 3. Erasure coding has the ability to reduce consumed storage capacity by fifty percent compared to data replication systems that store three copies of data. Nevertheless, erasure coding may also incur penalties such as processor overhead and write amplification.

As far as genomic data is concerned, no single data storage technique may be considered optimal for all data generated by a genomic pipeline. The genomic pipeline generates many different types of files, each with different access frequency and workload characteristics. Each stage of the genomic pipeline may generate different files, with some files being fed into successive stages while others being executed or generated by a single stage. Due to these differences, some files, or parts of those files, may be suited to a particular data storage technique while others may be more suited to another data storage technique in order to optimize the utilization of storage while providing adequate performance and/or redundancy. Thus, in certain embodiments, the most optimal solution may be to use a hybrid approach that utilizes several different data storage techniques. In certain cases, this hybrid approach may be used not only at the file level but at the intra-file level, such as at the block level. For example, certain parts (e.g., header, footer, data, metadata) of a file may be more suited to a first data storage technique while other parts may be more suited to another data storage technique.

Figure 4:
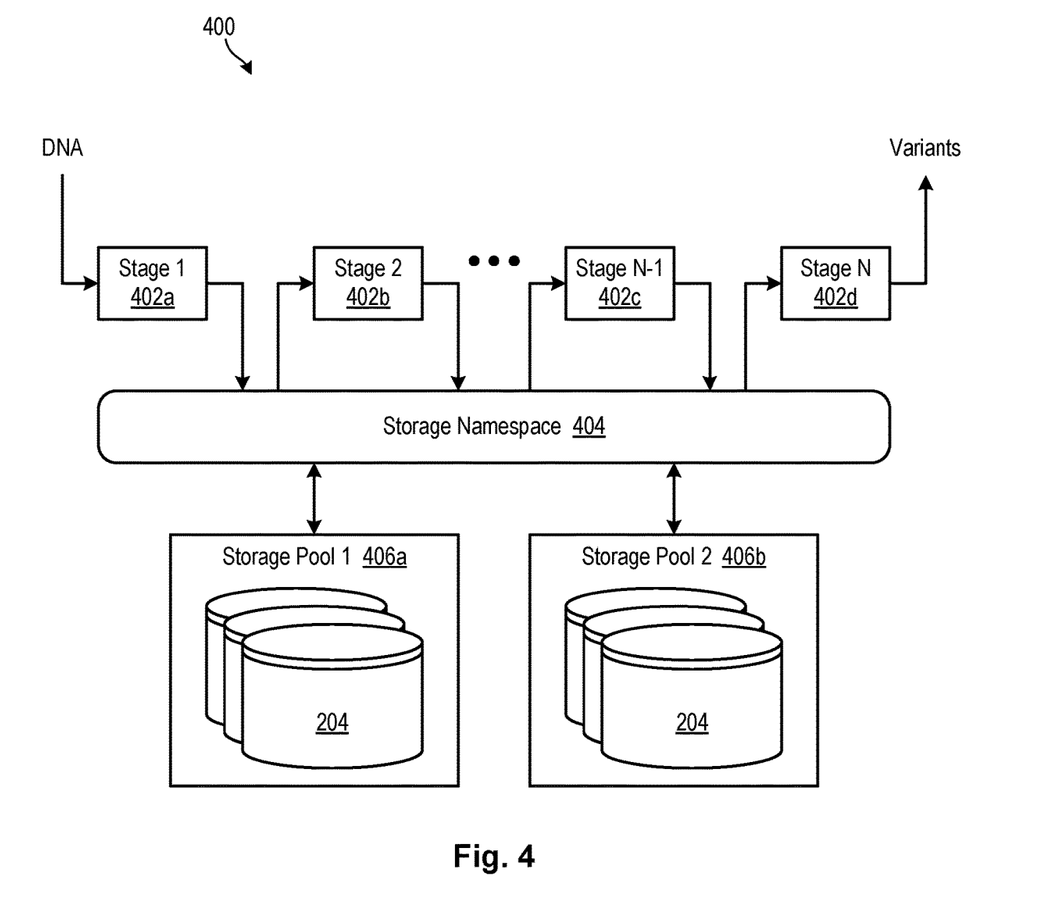
FIG. 4 is a high-level block diagram showing an example of a genomic pipeline.

Referring to FIG. 4, one example of a genomic pipeline 400 is illustrated. As previously mentioned, a typical genome pipeline 400 involves the following stages 402: collecting of sequencing output, quality assessment/control, genome assembly, read mapping, taxonomic investigation, variant calling, genome annotation, orthology and phylogeny, variant-of-interest, and sharing or visualization of results. Each stage 402 of the genomic pipeline 400 exhibits different data/metadata read and write characteristics as well as generates files of different types, sizes, and importance. These files may be used in subsequent stages 402 or may be discarded or retained after a single stage 402 is executed.

As further shown in FIG. 4, each of the stages 402 may access a storage namespace 404 that provides a uniform directory for accessing and storing files of the genomic pipeline 400. One or more storage pools 406, containing storage drives 204, may interface with the storage namespace 404 to store files associated with the genomic pipeline 400. Conventionally, a storage namespace 404 such as that illustrated in FIG. 4 is configured to use a single data storage technique, such as replication or erasure coding. However, a hybrid approach in accordance with the invention may be configured to utilize multiple different data storage techniques within a single storage namespace 404.

Figure 5:
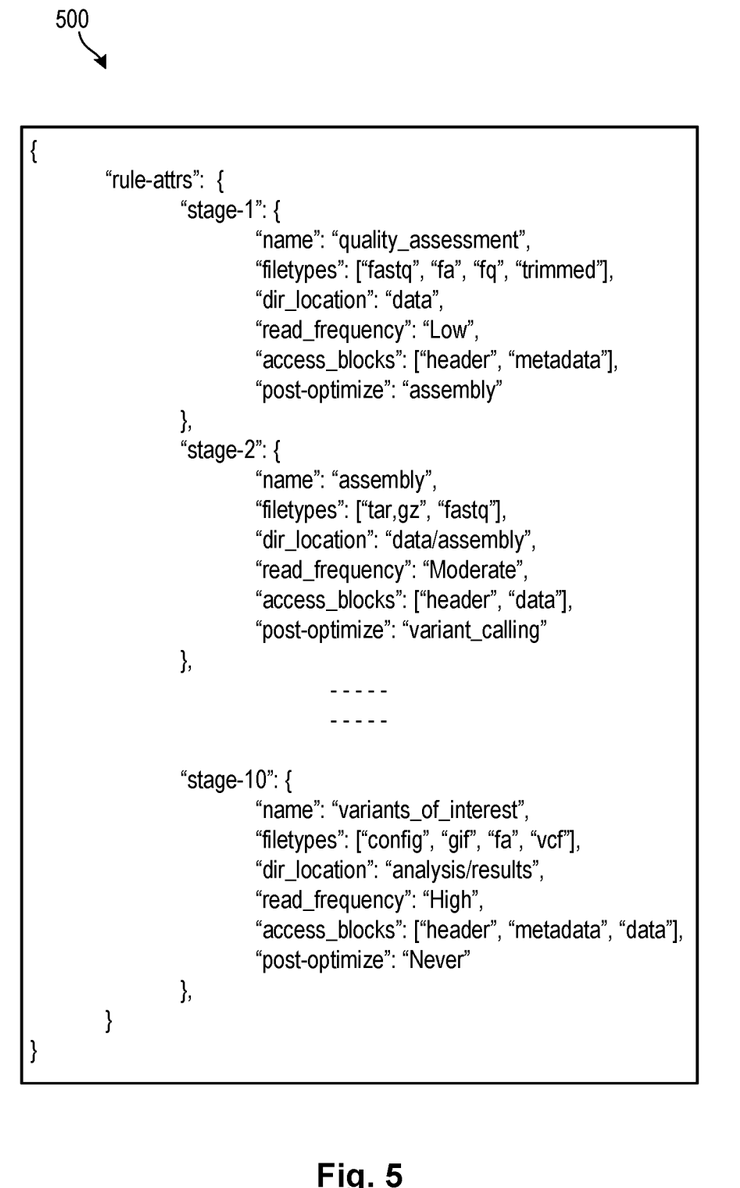
FIG. 5 is one example of a data structure storing a rules set.

Referring to FIG. 5, in order to implement a hybrid approach such as that described above, various rules may be formulated to determine when a particular data storage technique is to be used with particular files or blocks within the files. FIG. 5 shows one embodiment of a data structure 500 that may be used to represent such rules. This data structure 500 may be prepared by an administrator or, alternatively, populated from past statistics using machine learning techniques.

As shown in FIG. 5, the data structure 500 lists the various stages 402 (i.e., "stage-1", "stage-2", etc.) of the genomic pipeline 400 as well as attributes or properties associated with the stages 402. For example, each stage 402 may have a name, file types that are generated by the stage 402, a directory location where files generated by the stage 402 are stored, read frequency of files that are generated by the stage 402, and parts of files that are accessed the most (i.e., "access-blocks" field). The data structure 500 may also indicate the stage 402 after which the files should be optimized and stored using the most efficient data storage technique (i.e., "post-optimize" field). For example, a file 304 may be generated in stage-1, but actually be utilized in stage-3, and its optimal data storage technique may be erasure coding. In such a case, the optimal data storage technique may be applied to the file 304 after stage-3. Before the completion of stage-3, the file 304 may be stored using a default or intermediate data storage technique that is different than the optimal data storage technique. In short, the data structure 500 describes attributes of each stage 402, including I/O patterns, read frequency, and information about which subsequent stage consumes data produced by a particular stage 402.

Figure 6:
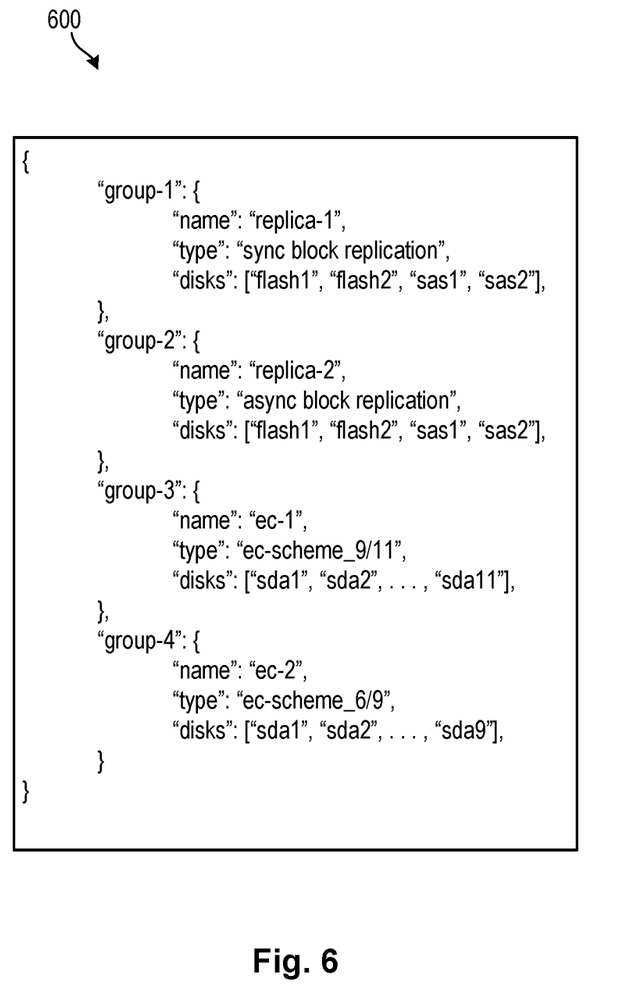
FIG. 6 is one example of a data structure that maps different data storage techniques to different storage drives.

Referring to FIG. 6, one example of a data structure 600 is shown that maps data storage techniques to various storage drives 204. As shown, a hybrid approach in accordance with the invention may include dividing storage under a single namespace 404 into multiple groups (i.e., "group-1", "group-2", etc.), where each group maps to various storage drives 204. Each group may use a different data storage technique to store and protect data. For example, "group-1" may use synchronous data replication to replicate data to a set of four storage drives 204, "group-2" may use asynchronous data replication to replicate data to a set of four storage drives 204, "group-3" may use a first erasure coding scheme to write data to eleven storage drives 204 while only requiring nine storage drives 204 to recover the data, and "group-4" may use a second erasure coding scheme to write data to nine storage drives 204 while only requiring six storage drives 204 to recover the data.

Figure 7:
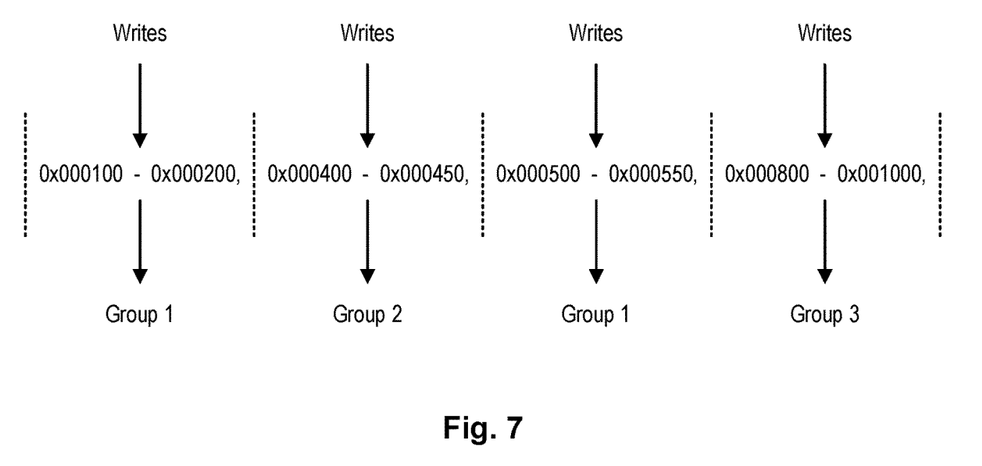
FIG. 7 shows writes to different address ranges being directed to different storage areas and data storage techniques.

Referring to FIG. 7, exemplary block ranges are shown for different storage groups, such as those discussed in association with FIG. 6. For example, writes to block range 0x000100-0x000200 may write data to storage group 1, writes to block range 0x000400-0x000450 may write data to storage group 2, writes to block range 0x000500-0x000550 may write data to storage group 1, writes to block range 0x000800-0x001000 may write data to storage group 3, and so forth. These block ranges are simply examples and are not intended to be limiting.

Figure 8:
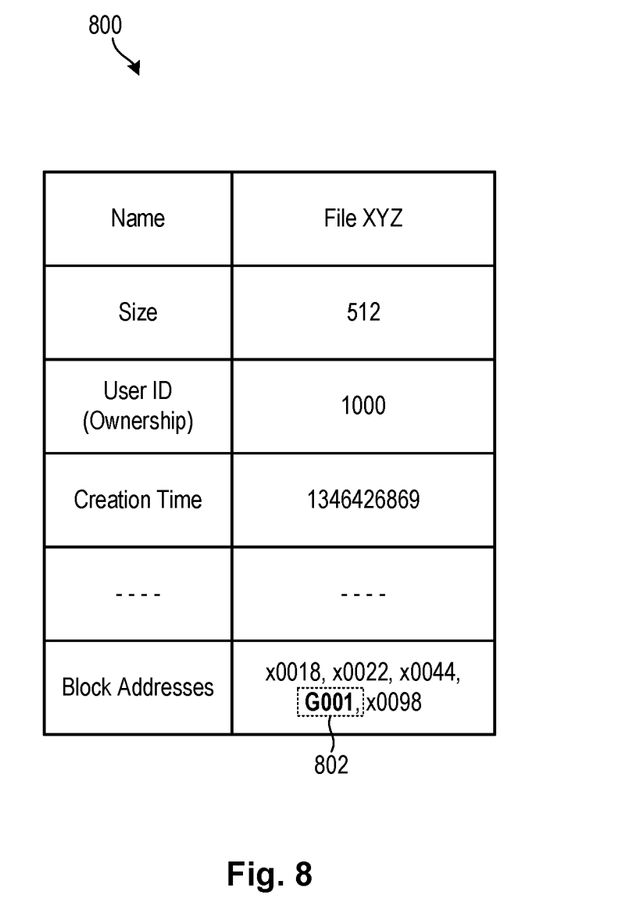
FIG. 8 shows one example of a modified inode data structure in accordance with the invention.
Figure 9:
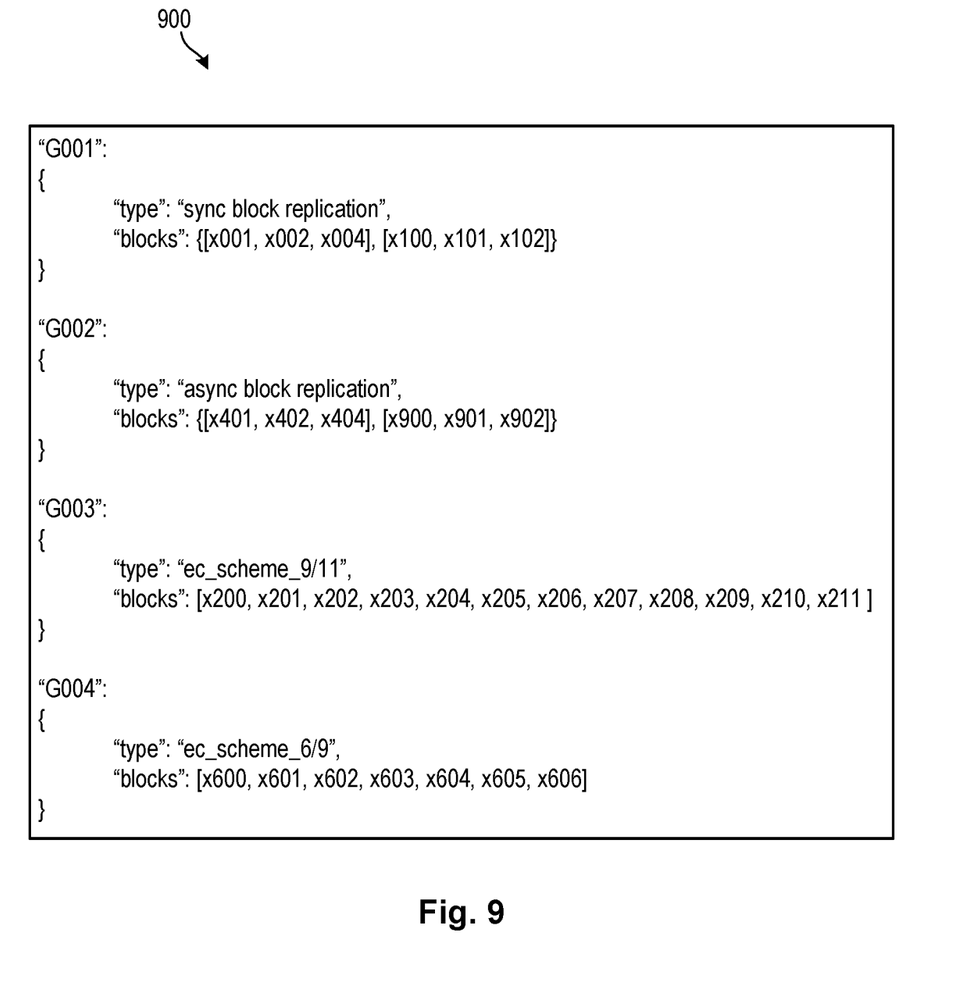
FIG. 9 is an example of a data structure mapping blocks to different storage groups.

Referring to FIG. 8, in certain embodiments, an inode structure 800 may be modified to use the hybrid approach disclosed herein. As can be appreciated by those skilled in the art, an inode 800 is a data structure that may be used to describe a file. The inode 800 may store attributes and block locations of the file's data. Attributes may include, for example, a file's name, size, user ID indicating the file's owner, creation time, and the like. The inode 800 may also list addresses of the file's data blocks. In certain embodiments in accordance with the invention, the inode 800 may be modified or adapted to include a storage group pointer 802 or identifier 802 that references a storage group in which blocks of the file are stored. The group pointer 802 or identifier 802 may be considered indirect in that it points to a data structure that point to blocks of the file's data. In certain embodiments, a separate data structure 900 may map the storage group pointer 802 or identifier 802 to one or more data blocks associated with the file. One example of such a data structure 900 is shown in FIG. 9. As shown in FIG. 9, storage group "G001" uses synchronous block replication as the data storage technique and maps to blocks x001, x002, x004, x100, x101, and x102. Storage groups using other data storage techniques and mapping to other blocks are also shown in the data structure 900 of FIG. 9.

Figure 10:
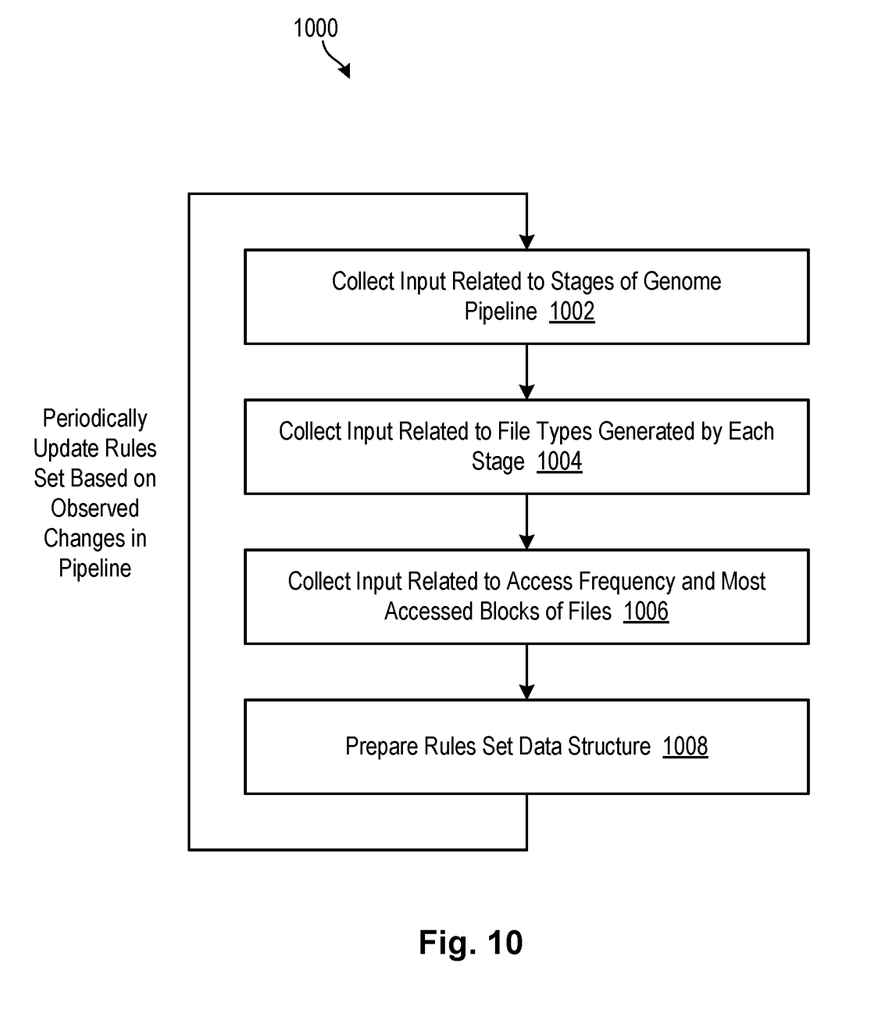
FIG. 10 is a flow diagram showing one embodiment of a method for preparing a rules set.

Referring to FIG. 10, one embodiment of a method 1000 for establishing a rules set in accordance with the invention is illustrated. Such a method 1000 may, in certain embodiments, be used to populate the data structure 500 of FIG. 5. As shown, the method 1000 collects 1002 input related to stages 402 of a genomic pipeline 400. This may include the names and order of the stages 402, directory locations where files generated by the stages 402 are stored, inputs and outputs of each of the stages 402, and the like. The method 1000 may further collect 1004 input related to the file types that are generated by each stage 402. The method 1000 may also collect 1006 input related to the access frequency and/or most highly accessed blocks or sections (e.g., header, footer, metadata, data, etc.) of files that are generated by the stages 402. The information from each of these steps 1002, 1004, 1006 may be manually received from an administrator or derived from past statistics using, for example, machine learning techniques. Using the information collected at steps 1002, 1004, and 1006, the method 1000 creates a data structure 500 containing the rules set. This data structure 500 may be periodically updated as changes to the genomic pipeline 400 are observed.

Figure 11:
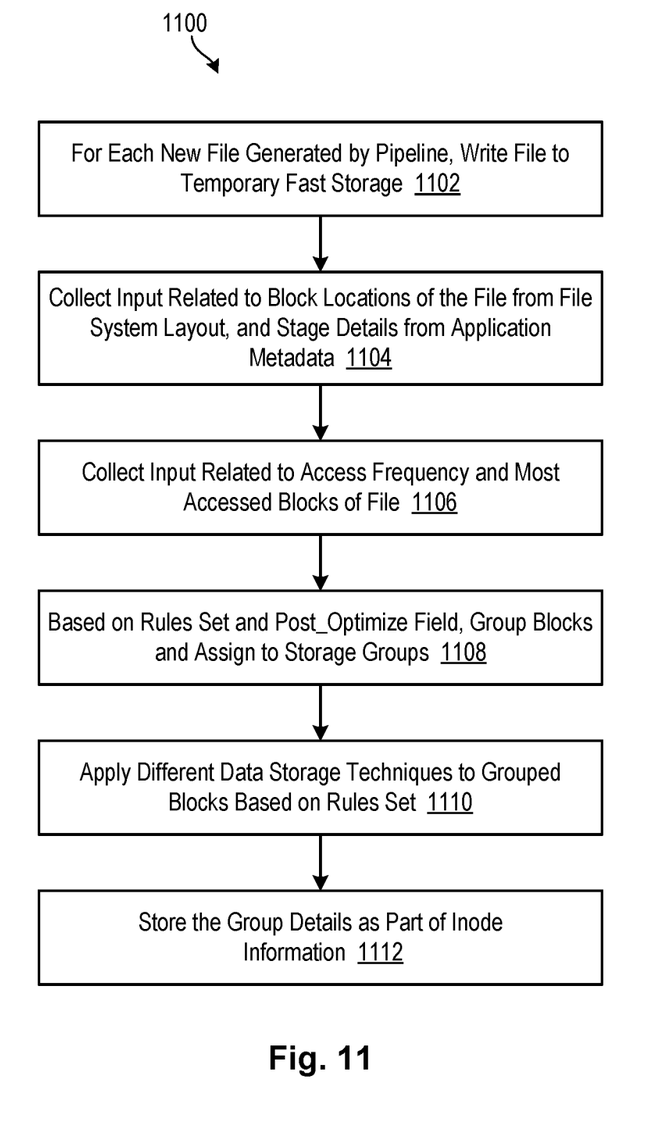
FIG. 11 is a flow diagram showing one embodiment of method for applying different data storage techniques to different blocks of a file.

Referring to FIG. 11, one embodiment of a method 1100 for applying different data storage techniques to different blocks of a file is illustrated. As shown, for each new file generated by the genomic pipeline 400, the method 1100 writes 1102 the file to temporary fast storage. The method 1100 then collects 1104 input related to the block locations of the file from a file system layout, and stages details of the file from application metadata. The method 1100 then collects 1106 input related to the access frequency and most accessed blocks of the file. Based on the rules set (as shown, for example, in FIG. 5) and the post optimize field, which indicates the stage 402 of the genomic pipeline 400 after which the file needs to be optimized, the method 1100 groups 1108 the blocks of the file and assigns the groups of blocks to storage groups, such as the storage groups illustrated in FIG. 6. The method 1100 may then apply 1110 the different data storage techniques to the grouped blocks in accordance with the rules set. The method 1100 may store the data storage details in the inode 800 of the file.

Figure 12:
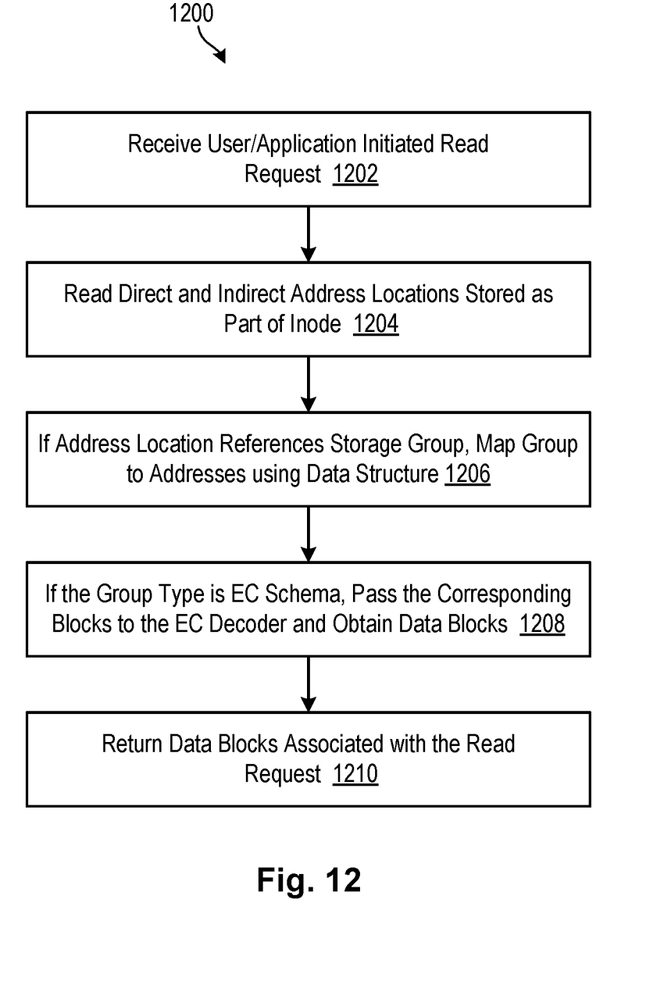
FIG. 12 is a flow diagram showing one embodiment of a method for processing a read request for a file stored using the hybrid approach disclosed herein.

Referring to FIG. 12, one embodiment of a method 1200 for processing a read request for a file that has been stored using the hybrid approach is illustrated. As shown, the method 1200 initially receives 1202 a user- or application-initiated read request. The method 1200 then reads 1204 direct and indirect address locations stored as part of the inode 800 of the file. If an address location identifies a storage group, the method 1200 maps 1206 the storage group to actual block storage locations using, for example, the data structure 900 illustrated in FIG. 9. If the storage group is of the erasure coding type, the method 1200 may pass 1208 the corresponding blocks to an erasure coding decoder to obtain the data blocks. The method 1200 then returns 1210 the data blocks associated with the read request.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other implementations may not require all of the disclosed steps to achieve the desired functionality. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The invention claimed is:

1. A method for more efficiently storing genomic data, the method comprising:
designating a plurality of different data storage techniques for storing genomic data generated by a plurality of stages of a genomic pipeline, wherein each stage of the plurality of stages generates different genomic data and exhibits different read/write characteristics;
generating a data structure comprising information associated with each of the plurality of stages and a rule set associated with each of the plurality of stages based at least on an input and an output of each stage;
identifying a file, made up of a plurality of blocks, generated by a stage of the plurality of stages of the genomic pipeline;
determining, based on the data structure, a data storage technique for each block of the file depending on whether the block contains data or metadata and whether the block will be input to another stage of the plurality of stages;
storing each block using its determined data storage technique after completion of a designated stage of the genomic pipeline, such that some blocks of the file are stored exclusively using a data replication technique mirroring the blocks across multiple locations, and other blocks of the file are stored exclusively using an erasure coding technique; and
iteratively updating the data structure based on one or more observed changes in the plurality of stages of the genomic pipeline.

2. The method of claim 1, wherein determining the data storage technique further comprises taking into account a file type associated with the file.

3. The method of claim 1, wherein determining the data storage technique further comprises taking into account the input of the stage of the plurality of stages of the genomic pipeline that generated the file.

4. The method of claim 1, wherein determining the data storage technique further comprises taking into account an access frequency associated with blocks of the file.

5. The method of claim 1, wherein determining the data storage technique further comprises taking into account which blocks of the file are most accessed.

6. The method of claim 1, wherein the data replication technique comprises at least one of a synchronous data replication technique and an asynchronous data replication technique.

7. The method of claim 1, wherein determining the data storage technique further comprises applying a rule set of the data structure to the file.

8. A computer program product for storing genomic data, the computer program product comprising a computer-readable storage medium having computer-usable program code embodied therein, the computer-usable program code configured to perform the following when executed by at least one processor:
designate a plurality of different data storage techniques for storing genomic data generated by a plurality of stages of a genomic pipeline, wherein each stage of the plurality of stages generates different genomic data and exhibits different read/write characteristics;
generate a data structure comprising information associated with each of the plurality of stages and a rule set associated with each of the plurality of stages based at least on an input and an output of each stage;
identify a file, made up of a plurality of blocks, generated by a stage of the plurality of stages of the genomic pipeline;
determine, based on the data structure, a data storage technique for each block of the file depending on whether the block contains data or metadata and whether the block will be input to another stage of the plurality of stages;
store each block using its determined data storage technique after completion of a designated stage of the genomic pipeline, such that some blocks of the file are stored exclusively using a data replication technique mirroring the blocks across multiple locations, and other blocks of the file are stored exclusively using an erasure coding technique; and
iteratively update the data structure based on one or more observed changes in the plurality of stages of the genomic pipeline.

9. The computer program product of claim 8, wherein determining the data storage technique further comprises taking into account a file type associated with the file.

10. The computer program product of claim 8, wherein determining the data storage technique further comprises taking into account the input of the stage of the plurality of stage of the genomic pipeline that generated the file.

11. The computer program product of claim 8, wherein determining the data storage technique further comprises taking into account an access frequency associated with blocks of the file.

12. The computer program product of claim 8, wherein determining the data storage technique further comprises taking into account which blocks of the file are most accessed.

13. The computer program product of claim 8, wherein the data replication technique comprises at least one of a synchronous data replication technique and an asynchronous data replication technique.

14. The computer program product of claim 8, wherein determining the data storage technique further comprises applying a rule set of the data structure to the file.

15. A system for storing genomic data, the system comprising:
   at least one processor;
   at least one memory device operably coupled to the at least one processor and storing instructions for execution on the at least one processor, the instructions causing the at least one processor to:
      designate a plurality of different data storage techniques for storing genomic data generated by a plurality of stages of a genomic pipeline, wherein each stage of the plurality of stages generates different genomic data and exhibits different read/write characteristics;
      generate a data structure comprising information associated with each of the plurality of stages and a rule set associated with each of the plurality of stages based at least on an input and an output of each stage;
      identify a file, made up of a plurality of blocks, generated by a stage of the plurality of stages of the genomic pipeline;
      determine, based on the data structure, a data storage technique for each block of the file depending on whether the block contains data or metadata and whether the block will be input to another stage of the plurality of stages;
      store each block using its determined data storage technique after completion of a designated stage of the genomic pipeline, such that some blocks of the file are stored exclusively using a data replication technique mirroring the blocks across multiple locations, and other blocks of the file are stored exclusively using an erasure coding technique; and
      iteratively update the data structure based on one or more observed changes in the plurality of stages of the genomic pipeline.

16. The system of claim 15, wherein determining the data storage technique further comprises taking into account a file type associated with the file.

17. The system of claim 15, wherein determining the data storage technique further comprises taking into account the input of the stage of the plurality of stage of the genomic pipeline that generated the file.

18. The system of claim 15, wherein determining the data storage technique further comprises taking into account an access frequency associated with blocks of the file.

19. The system of claim 15, wherein determining the data storage technique further comprises taking into account which blocks of the file are most accessed.

20. The system of claim 15, wherein the data replication technique comprises at least one of a synchronous data replication technique and an asynchronous data replication technique.

* * * * *